(12) United States Patent
Suzuki et al.

(10) Patent No.: US 10,041,887 B2
(45) Date of Patent: Aug. 7, 2018

(54) LITHIUM REAGENT COMPOSITION, AND METHOD AND DEVICE FOR QUANTIFYING LITHIUM IONS USING SAME

(71) Applicant: METALLOGENICS Co., Ltd., Chiba, Chiba (JP)

(72) Inventors: Hiroko Suzuki, Chiba (JP); Takuya Iwabuchi, Chiba (JP); Kazuhiro Koide, Chiba (JP); Tsugikatsu Odashima, Ichinoseki (JP)

(73) Assignee: METALLOGENICS Co., Ltd, Chiba, Chiba (JP)

( * ) Notice: Subject to any disclaimer, the term of this patent is extended or adjusted under 35 U.S.C. 154(b) by 30 days.

(21) Appl. No.: 15/102,309

(22) PCT Filed: Nov. 11, 2014

(86) PCT No.: PCT/JP2014/079806
§ 371 (c)(1),
(2) Date: Jun. 7, 2016

(87) PCT Pub. No.: WO2015/087650
PCT Pub. Date: Jun. 18, 2015

(65) Prior Publication Data
US 2017/0003228 A1  Jan. 5, 2017

(30) Foreign Application Priority Data
Dec. 9, 2013 (JP) .................................. 2013-254196

(51) Int. Cl.
*G01N 21/78* (2006.01)
*G01N 31/22* (2006.01)
*C07D 487/22* (2006.01)

(52) U.S. Cl.
CPC ........... *G01N 21/78* (2013.01); *C07D 487/22* (2013.01); *G01N 31/22* (2013.01)

(58) Field of Classification Search
CPC .............................. G01N 21/78; G01N 31/22
See application file for complete search history.

(56) References Cited

FOREIGN PATENT DOCUMENTS

JP          2014095567       * 11/2012

* cited by examiner

*Primary Examiner* — Krishnan S Menon
*Assistant Examiner* — Dwan A Gerido
(74) *Attorney, Agent, or Firm* — Sughrue Mion, PLLC

(57) ABSTRACT

A lithium reagent composition for determining lithium concentration, with which it is possible to instantaneously determine the amount of lithium contained in an aqueous solution, such as a biosample or an environmental sample, by means of a simple colorimeter or ultraviolet-visible spectrophotometer and which renders a visual assessement possible; and a method and device for quantifying lithium ions using the composition. A lithium reagent composition obtained by mixing the compound represented by the structural formula, wherein all of the hydrogen atoms bonded to carbon atoms of tetraphenylporphyrin have been replaced with fluorine atoms, as a chelating agent with a basic organic compound selected from monoethanolamine, diethanolamine, and triethanolamine and producing an aqueous solution thereof that further contains a pH regulator with which the pH has been regulated to 5 or higher; and a method and device for quantifying lithium ions using the composition.

(Continued)

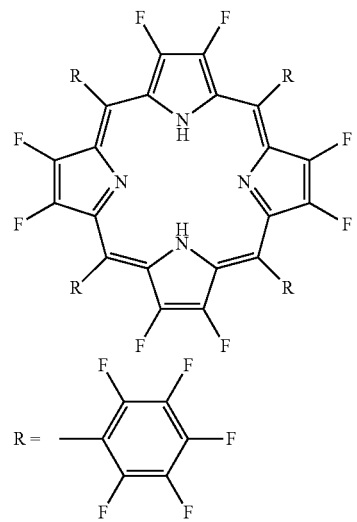
(I)
11 Claims, 5 Drawing Sheets

[Fig.1]
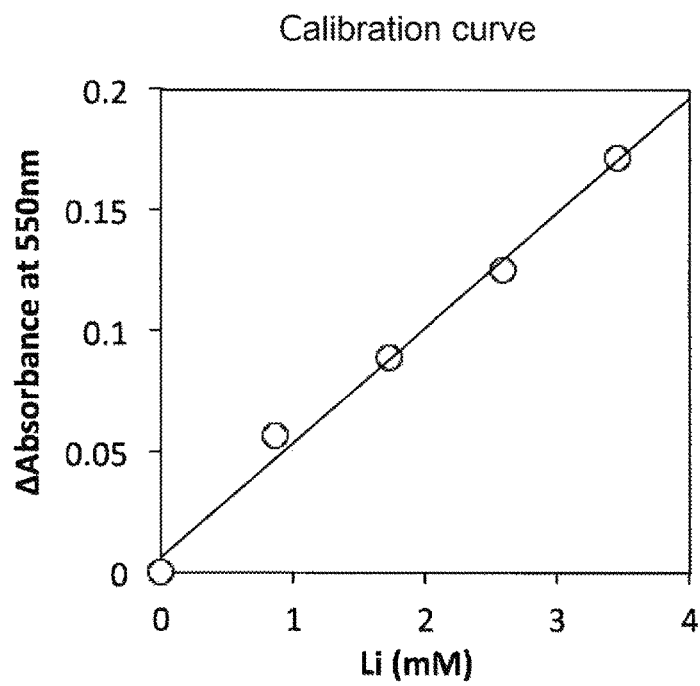
[Fig.2]
[Table 1]
| Control serum | A (Prior art) | B (No solvent) | C (Example 1) | D (atomic absorption method) |
|---|---|---|---|---|
| Pathonorm H | 1.54 | Sensitivity zero | 1.52 | 1.54 |
| Seronorm | 0.97 | Sensitivity zero | 1.01 | 1.00 |
| Seronorm human | 0.76 | Sensitivity zero | 0.72 | 0.74 |
UNIT : mM

[Fig.3]
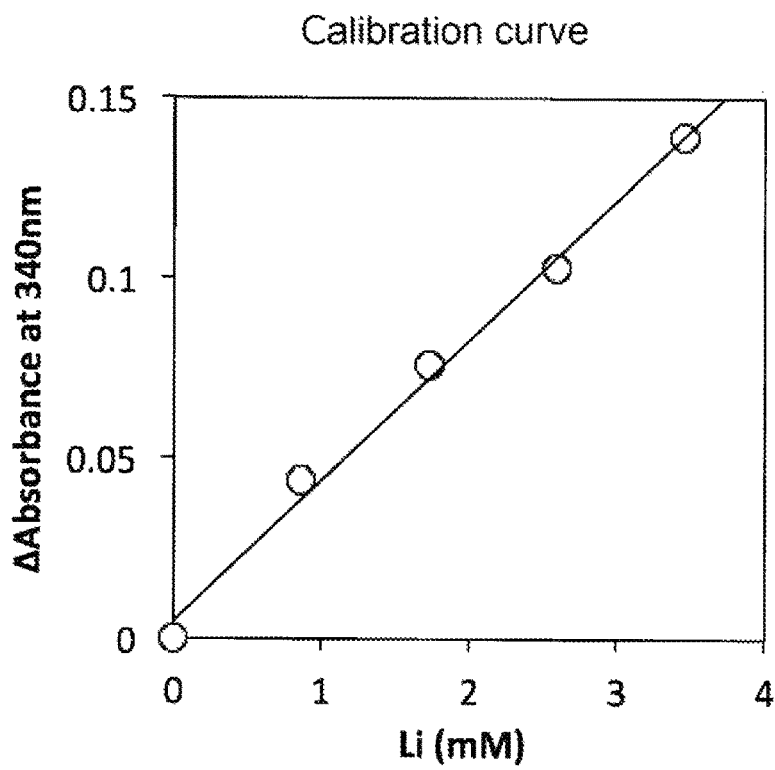
[Fig.4]
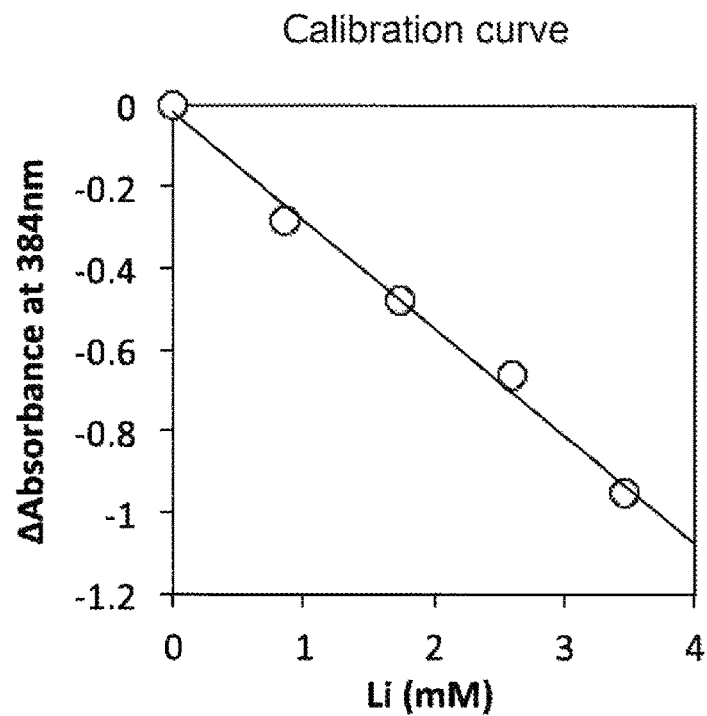

【Fig.5】
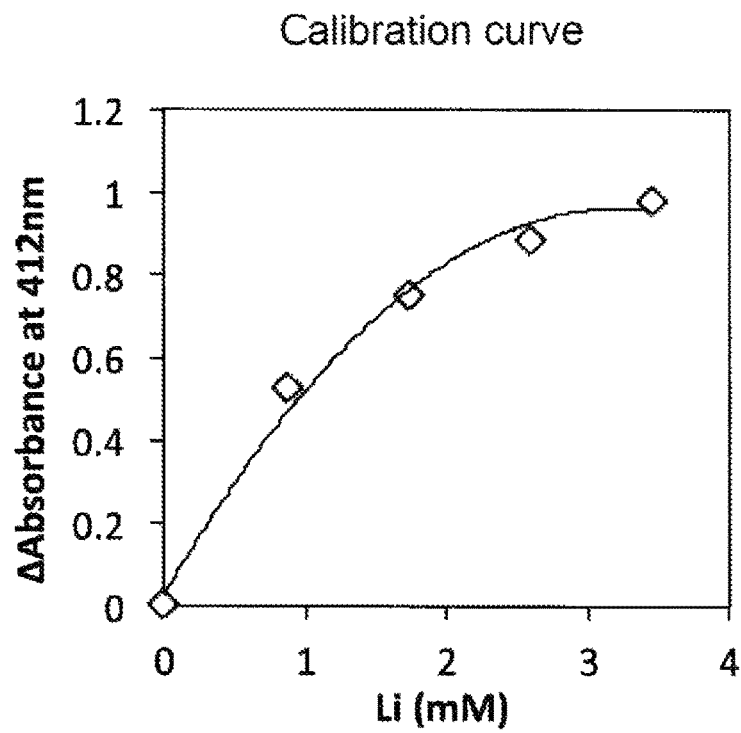
【Fig.6】
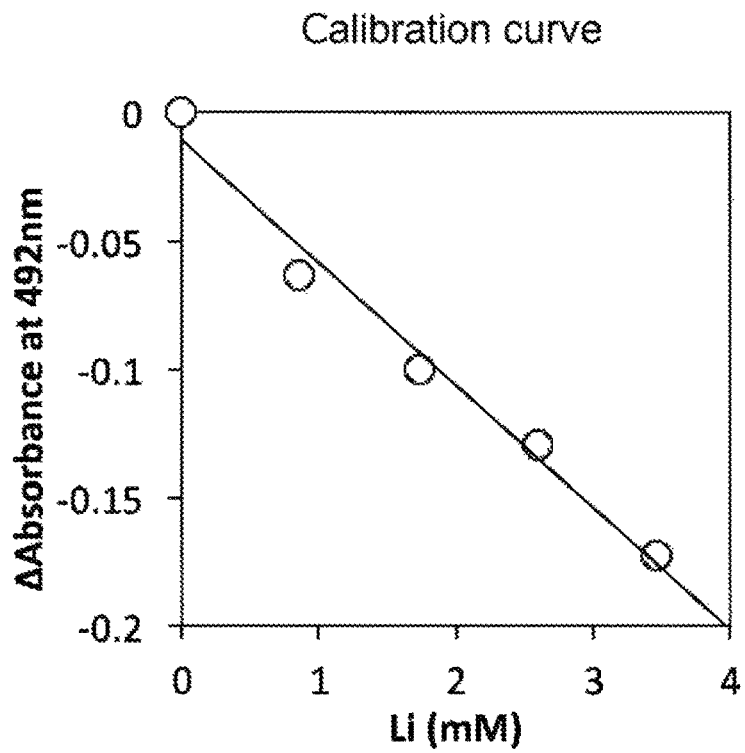

[Fig.7]
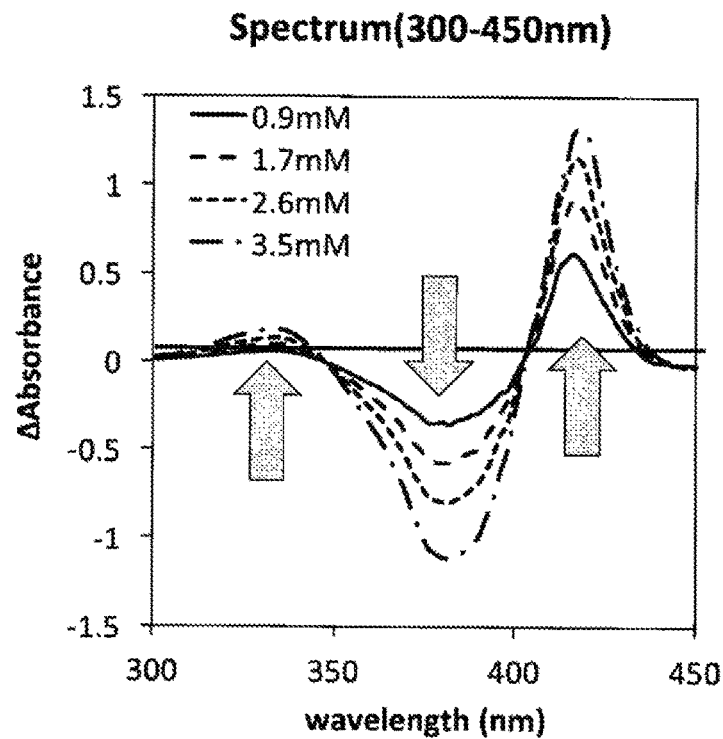
[Fig.8]
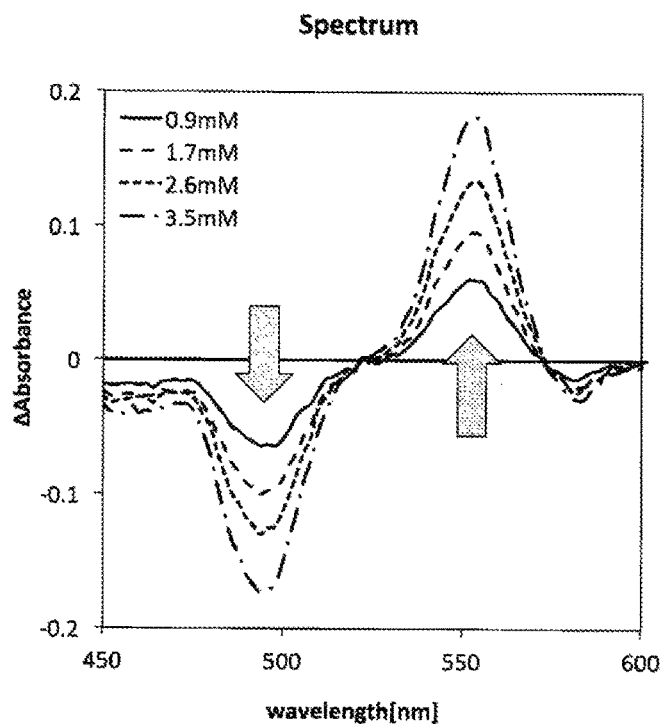

[Fig.9]
【Table 2】
| Control serum | Guaranteed value | Measured value in Example 1 |
|---|---|---|
| Pathonorm L | 0 | 0 |
| Pathonorm H | 1.54 | 1.52 |
| Seronorm human | 0.76 | 0.78 |
Unit.: mM
[Fig.10]
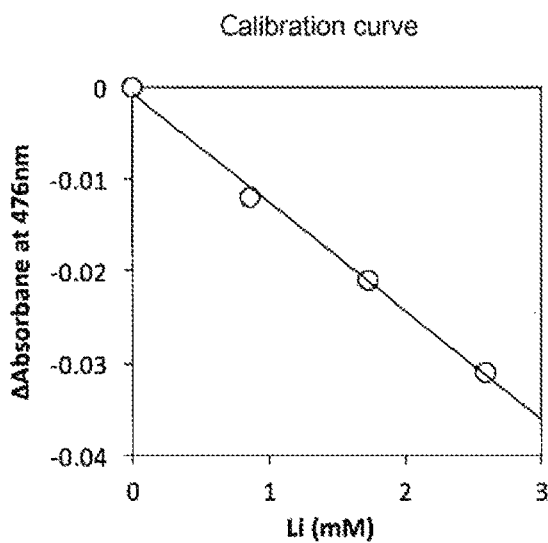
[Fig.11]
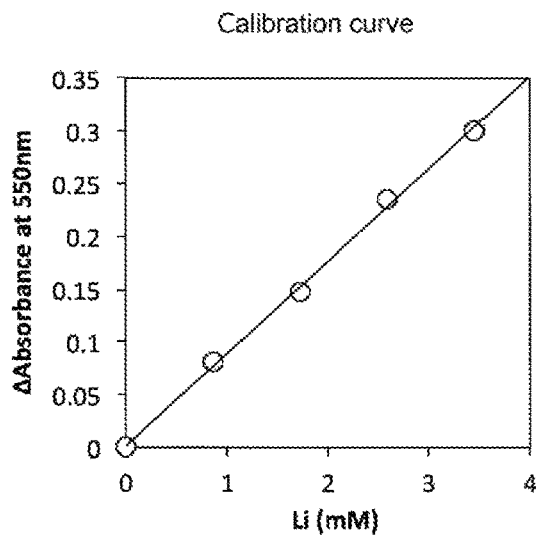

LITHIUM REAGENT COMPOSITION, AND METHOD AND DEVICE FOR QUANTIFYING LITHIUM IONS USING SAME

CROSS REFERENCE TO RELATED APPLICATIONS

This application is a National Stage of International Application No. PCT/JP2014/079806, filed Nov. 11, 2014, claiming priority based on Japanese Patent Application No. 2013-254196, filed Dec. 9, 2013, the contents of all of which are incorporated herein by reference in their entirety.

TECHNICAL FIELD

This invention relates to a reagent composition used in quantitative measurement of lithium in aqueous solutions such as biological specimens and environmental liquid samples, and to a measuring method and device for determining a quantity of lithium ion by using the reagent composition.

BACKGROUND ART

It is known that lithium-containing drugs are effective drugs for feeling stabilization and antidepressant, so that they are used widely as feeling-stabilizer and antidepressant drug.

However, it is necessary to control the concentration of lithium in serum within a proper range when the lithium-containing drug is administrated to patients.

As feeling stabilizer, tablets of lithium carbonate (for oral administration) are generally prescribed together with another drug for bipolar disorder (circulatory psychosis) or anti-depressive drug. Lithium carbonate ($Li_2CO_3$) has such a characteristic that its administration effect is exhibited only when a concentration of lithium in blood arrives at nearly a lithium poisoning level. Therefore, the therapeutic drug monitoring (TDM) is prescribed to monitor the lithium concentration in blood when the drug is administrated, since a therapeutic range is very near to the poison level.

In practice, it is necessary to control or limit the concentration of lithium in a patient blood sample within a range of from 0.6 to 1.2 mEq/L in general. In fact, when the lithium concentration in serum is lower than 0.6 mEq/L, no antidepressive effect is expected. On the contrary, excess administration over 1.5 mEq/L concentration in plasma will result in the lithium poisoning. Overdose result in a fatal cause of symptom of poisoning including tremor, aralia, nystagmus, renal disturbance and convulsion. Therefore, when a sign of latently dangerous symptom of poisoning is observed, the treatment with lithium-containing drugs must be stopped and it is necessary to re-measure the concentration in plasma and to take measures to mitigate the lithium poisoning.

Thus, the lithium salt is an effective medicine in treatment of depression patients, but overdose thereof result in serious troubles. Therefore, when a lithium-containing anti-depressive drug is administered, it is indispensable to monitor the concentration of lithium in serum and to assure that the concentration is always kept in a limited range of from 0.6 to 1.2 mEq/L.

Therefore, it was requested to carry out the quantitative measurement of lithium in serum in the treatment of depression patient, and several liquid reagent compositions permitting colorimetric determination of lithium for clinical laboratory test have been developed.

Patent Document 1 discloses a reagent composition used to determine the concentration of lithium in a biological sample by using primary color body cryptideinofa.

Patent Document 2 discloses an analytical reagent which reacts with lithium ions, comprising a macrocyclic compound having a pyrrole ring and eight bromine (Br) atoms bonded at β position of the pyrrole ring.

Non-Patent Document 1 discloses that lithium ions can be detected by a compound in which all hydrogens bonded to carbons of tetraphenylporphyrin are replaced by fluorine.

Known lithium reagent compositions, however, have such demerits or problems that they are poisonous compositions, that drug substances are expensive or are not supplied stably and that most drug substances do not dissolve in water or, even soluble, and are deactivated in water, so that coloring reaction is very slow.

In Patent Document 2 which was developed to solve the above problems, a color developing technique can be used but it is necessary to dilute specimens because its sensibility is too high. Still more, this lithium reagent composition requires a pH range of over 11 and hence tends to be deteriorated with $CO_2$ in air, so that the resulting measured data are not stable. Still more, in a range of over pH11, only sodium hydroxide and potassium hydroxide can be used to prepare practical concentrated aqueous solution and there is no other compounds which can be used actually, so that it is difficult to keep a constant pH value. Still more, these concentrated aqueous solutions are hazardous substances which are difficult to be handled, so that their use should be avoided. Du to these demerits, a special container is necessary and a large special equipment or installation is required in their handling, so that they are not suitable for general uses. Therefore, this technology has such a problem that it is difficult to apply to on-site monitoring and POCT (Point Of Care Testing).

In Patent Document 1, a compound which is completely different from the compound of this invention (which will be explained later) is used in a reagent composition for measuring a quantity of lithium. The compound of Patent Document 1 can be used only at pH 12. As stated above, in a range of over pH 11, there is no other practical concentrated aqueous solution than those of sodium hydroxide and of potassium hydroxide. And hence, the reagent composition of Patent Document 1 have no versatility because the above aqueous solution is hazardous substance which are difficult to be handled and a large special equipment or installation is required in their practical uses.

In the non-Patent Document 1, Koyanagi et al. disclose that lithium ions can be separated and detected by using F28 tetraphenylporphyrin. However, solvent extraction with oily poisonous chloroform is necessary to perform the separation and detection of lithium ions. Above all, direct determination of lithium in an aqueous solution could not be carried out without complicated pretreatment or handling.

Thus, there was such a problem that lithium ions in serum can't be measured rapidly and quantitatively in practical method. In fact, the quantitative measurement of lithium ions in aqueous solutions by using F28 tetraphenylporphyrin was difficult to be realized, so that the concentration of lithium ions could not be determined quantitatively in practical method.

The present inventors developed in Patent Document 3 (Japanese Patent No. 5,222,432) a reagent composition for lithium ("lithium reagent composition" hereafter), comprises a compound having a structure represented by the formula (I), as chelating agent:

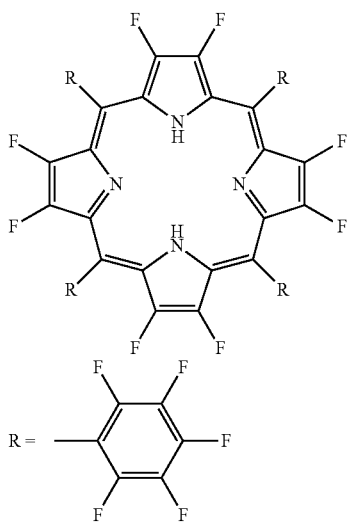

(I)

in which all hydrogens bonded to carbons of a tetraphenylporphyrin are replaced by fluorine, a water-soluble organic solvent, a pH modifier and a stabilizer, and a method for measuring lithium by using the same, so that the lithium concentration in biological specimens and environmental liquid samples can be measured immediately and quantitatively by the convenient colorimeter or ultraviolet-visible light spectrophotometer. The present inventors provided also a lithium reagent composition which permits to determine the lithium concentration quantitatively and method and apparatus for measuring lithium ion using the same.

PRIOR ARTS

Patent Document

Patent Document 1 JP-A1-7-113807
Patent Document 2 EP1283986-B1
Patent Document 3 Japanese Patent No. 5,222,432
Non-Patent Document 1 Analytical Chemistry Vol. 51, No. 9, pp. 803-807 (2002); K. Koyanagi et al., "Synthesis of F28 tetraphenylporphyrin and its use for separation and detection"

SUMMARY OF INVENTION

Problems to be Solved by the Invention

As stated above, the invention of Patent Document 3 permits to measure lithium in aqueous solutions such as biological specimens and environmental liquid samples quantitatively and immediately by using a small colorimeter and of a ultraviolet-visible light spectrophotometer. Thus, Patent Document 3 provides a reagent composition for effecting the quantitative measurement of lithium by naked eyes as well as a method and apparatus for measuring lithium ion by using the reagent composition comprising a compound having the structure in which all hydrogens bonded to carbons of a tetraphenylporphyrin are replaced by fluorine, as chelating agent added with a water-soluble organic solvent such as dimethyl sulfoxide (DMSO), dimethyl formamide (DMF) and dimethyl acetamide (DMA).

The invention of Patent Document 3, however, had a problem to be solved. Namely, it is advisable to avoid use of the organic solvent if possible because the organic solvent is absorbed through skin, mucous membrane and lung and will be a cause of poisoning or disorder or give an adverse effects on health. And, to reduce the loads on the environment at disposal of the organic solvent, use of the organic solvent should be avoided.

Therefore, a problems to be solved by the Invention is to provide a reagent composition for lithium ("lithium reagent composition") without using the organic solvent such as dimethyl sulfoxide (DMSO), dimethyl formamide (DMF) and dimethyl acetamide (DMA). Thus, the present invention provides a lithium reagent composition comprising the compound having the above structure (I) in which all hydrogens bonded to carbons of a tetraphenylporphyrin are replaced by fluorine for measuring lithium in aqueous solutions such as biological specimens and in environmental liquid samples quantitatively and immediately by using a simple colorimeter or a ultraviolet-visible light spectrophotometer. The present invention provides also a reagent composition which permits quantitative measurement of lithium by naked eyes as well as a method and apparatus for measuring lithium ion by using the same.

Means to Solve the Problems

To solve the above problem, the present invention provides a lithium reagent composition, characterized in that it is in a form of an aqueous solution comprising a compound having a structure represented by the formula (I):

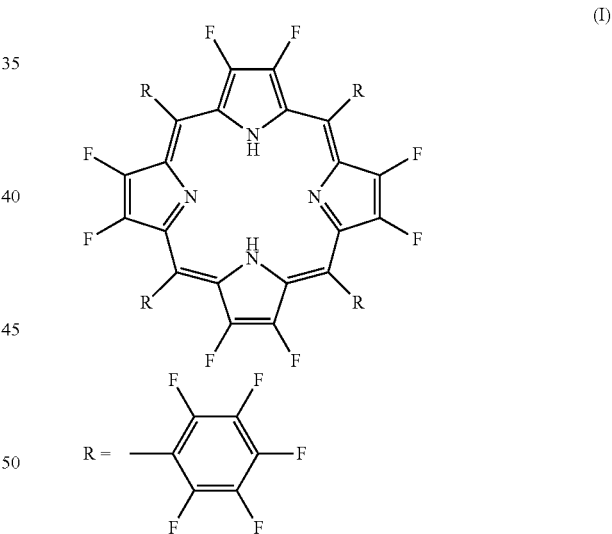

(I)

in which all hydrogens bonded to carbons of a tetraphenylporphyrin are replaced by fluorine atoms, mixed with a basic organic compound selected from the group comprising monoethanol amine, di-ethanol amine and tri-ethanol amine, and a pH modifier for adjusting the pH of the solution higher than pH 5.

In the present invention, lithium in an aqueous solution such as a biological specimen and an environmental sample generates a color by the lithium reagent composition according to the present invention, in particular by the compound in which all hydrogens bonded to carbons of a tetraphenylporphyrin are replaced by fluorine, which functions as a chelating reagent (color developer).

Color change from yellow to red by a coloring reaction which is observed between a F28 tetraphenylporphyrin compound and lithium ions is difficult to be realized. However, what is requested is to determine precisely a quantity of lithium in serum in a range of 0.6 mg/dL to 2.0 mg/dL (0.9 mM to 3 mM). In an embodiment of this invention, inventors found such a fact that the quantity of lithium in serum can be determined precisely by setting a concentration of the F28 tetraphenylporphyrin compound in a range of 0.05 to 1.0 g/L, preferably 0.5 g/L.

In the lithium reagent composition according to the present invention, the pH modifier is used. The F28 tetraphenylporphyrin compound which is a color developer (chelating reagent) according to this invention does not bond to lithium ion in an acidic side lower than pH 5.0, and hence no coloration change is observed so that it is difficult to determine the quantity of lithium.

A specific reaction between the color developer and lithium ion occurs in a range between pH 5 and pH 7, but the coloring reaction speed is slow. In a range between pH 8 and pH 11, the color developer reacts with lithium ion rapidly and a stable coloring complex can be formed. In alkaline side of higher than pH 11, a color tone of the chelating reagent and of coloring complex formed becomes instable in time. This may be caused by absorption of carbon dioxide in air and a pH value fluctuates. Therefore, it is necessary to use a pH modifier or pH buffer that can keep the pH of lithium reagent composition according to the present invention in a range from pH 8 to pH 11.

The pH modifier can be selected from alkali medicine including sodium hydroxide, potassium hydroxide and ammonia, acid medicine including acetic acid, phosphoric acid, citric acid, carbonic acid, bicarbonic acid, oxalic acid, hydrochloric acid, nitric acid and their salts. The pH modifier may be pH buffer and may be selected from citric acid, carbonic acid, bicarbonic acid, phosphoric acid, succinic acid, phthalic acid, ammonium chloride, sodium hydroxide, potassium hydroxide, MES as Good's buffer, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, CAPS and their salts.

The lithium reagent composition according to the present invention incorporating the pH modifier permits the specific color reaction for lithium in a range of from pH 5 to pH 11.

When the concentration of lithium in sample is determined by a general-purpose type automated analyzer and by an ultraviolet-visible light spectrophotometer, it is desirable that the reagent composition is in a form of an aqueous solution, since a test sample to be measured is in a form of an aqueous solution. Therefore, the lithium reagent composition according to the present invention is dissolved in water to form a solution which compatible with an aqueous solution of a test sample such as serum, blood plasma and eluate.

According to the present invention, the F28 tetraphenylporphyrin compound is dissolved in water in the presence of a basic organic compound selected from monoethanol amine, di-ethanol amine and tri-ethanol amine in place of the organic solvent.

In actual products, a suitable stabilizer is incorporated in the reagent composition according to this invention. In an embodiment, a surfactant is used as the stabilizer. The surfactant improves the dispensability of F28 tetraphenylporphyrin compound and prevents formation of suspensions originated from the sample during the coloring reaction. Therefore, the stabilizer is used to assure such effect.

The stabilizer may be nonionic surfactant or anionic surfactant. The nonionic surfactant may be sorbitan fatty acid ester, pentaerythritol fatty acid part ester, propylene glycol monofatty acid ester, glycerin fatty acid monoester, polyoxyethylene alkyl ether, polyoxyethylene alkyl phenyl ether, polyoxyethylene polyoxypropylene glycol, polyoxyethylene fatty acid part ester, polyoxyethylene sorbitol fatty acid part ester, polyoxyethylene fatty acid ester, fatty acid di-ethanol amide, fatty acid ethanol amide, polyoxyethylene fatty acid amide, polyoxyethylene octylphenyl ether (Triton X-100®), p-nonyl phenoxy polyglycidol or their salts.

Preferable nonionic surfactants are polyoxyethylene octylphenyl ether (Triton X-100®) and p-nonyl phenoxy polyglycidol.

The anionic surfactant as stabilizer may be alkyl sulfate ester salt, polyoxyethylene alkyl ether sulfate salt, polyoxyethylene phenyl ether sulfate salt, alkyl benzenesulfonate and alkanesulfonate. Typical anionic surfactant is selected from sodium dodecyl sulfate, sodium dodecyl benzenesulfonate, sodium polyoxyethylene alkylphenyl ether sulfate and their salts.

The lithium reagent composition according to the this invention may contain more than one masking reagent, in order to avoid disturbance caused by other ions than lithium which may present in the sample, to suppress oxidation of the reagent composition and to improve the storage stability. The masking reagent may be not necessary if there are few ions other than lithium.

The masking reagent which can be added to the lithium reagent composition according to the present invention may be selected from ethylenediamine, N,N,N',N'-tetrakis(2-pyridylmethylethylenediamine (TPEN), pyridine, 2,2-bipyridine, propylene diamine, dimethylene triamine, dimethylene triamine-N,N,N',N'',N'''-penta acetic acid (DTPA), trimethylene tetramine, trimethylene tetramine-N,N,N',N'', N''',N''''-hexa acetic acid (TTHA), 1,10-phenanthroline, ethylene diamine tetra acetic acid (EDTA), O,O'-bis(2-aminophenyl)ethyleneglycol-N,N',N'-tetra acetic acid (BAPTA), N,N-bis(2-hydroxyethyl)glycine (Bicine), trans-1,2-diaminocyclohexane-N,N,N',N'-tetra acetic acid (CyDTA), O,O'-bis(2-aminoethyl) ethyleneglycol-N,N,N',N'-tetra acetic acid (EGTA), N-(2-hydroxyl) imino diacetic acid (HIDA), imino diacetic acid (IDA), nitrile triacetic acid (NTA), nitrile trimethylphosphonate (NTPO) and their salts.

The lithium reagent composition according to this invention may include antiseptics to prevent degradation caused by microorganism. The antiseptics are not limited especially and may be sodium azide and Procline®. An amount of antiseptics is not especially limited and may be a concentration used generally as an antiseptic. For example, in case of sodium azide, the amount of antiseptics is about 0.1% by mass to a reaction solution. The antiseptics are usually prescribed for products which are stored for longer term duration.

In actual uses, the lithium reagent composition according to the present invention is contacted with a test sample of serum and/or blood plasma to induce coloring of lithium complex. The resulting color development or the absorbance and spectrum of the lithium complex is measured to determine a quantity of lithium in the sample by comparing with reference concentrations of a standard sample whose lithium concentrations are of known.

In practice, in the coloring and the spectrum, the sensitivity is measured preferably at a wavelength of 550 nm or in the vicinity of wavelength from 530 nm to 560 nm, or the sensitivity is measured at a wavelength of 570 nm or in the vicinity of wavelength from 565 nm to 650 nm, or the sensitivity is measured at a wavelength of 340 nm or in the vicinity of wavelength from 310 nm to 350 nm, or the sensitivity is measured at a wavelength of 380 nm or in the vicinity of wavelength from 350 nm to 400 nm, or the sensitivity is measured at a wavelength of 476 nm or in the vicinity of wavelength from 460 nm to 510 nm, to calculate the concentration of lithium. In this case, the sensitivity is understood as the absorbance or a difference in absorbance in an ultraviolet-visible light spectrophotometer.

In order to cancel out an influence of hemoglobin, the sensitivity at a wavelength of 550 nm can be corrected by the following equation:

> The sensitivity at a wavelength of 550 nm=the sensitivity at a wavelength of 550 nm for lithium-F28 tetraphenylporphyrin complex+the sensitivity at a wavelength of 550 nm for hemoglobin−the sensitivity at a wavelength of 600 nm for hemoglobin The above sensitivity at a wavelength of 600 nm for hemoglobin is a preferable correction value for the cancel out. However, it is possible to use another value of in the vicinity of wavelength of 600 nm which can be the similar sensitivity ratio to the sensitivity at a central wavelength of 550 nm.

In the measuring device, the color development, absorbance or spectrum of the lithium complex generated from the lithium reagent composition according to the present invention contacted with a test sample of serum and blood plasma is measured. In practice, the sensitivity at a wavelength of 550 nm or in the vicinity of wavelength from 530 nm to 560 nm in the spectrum is measured, or the sensitivity at a wavelength of 570 nm or in the vicinity of wavelength from 565 nm to 650 nm is measured, or the sensitivity at a wavelength of 340 nm or in the vicinity of wavelength from 310 nm to 350 nm is measured, or the sensitivity at a wavelength of 380 nm or in the vicinity of wavelength from 350 nm to 400 nm is measured, or the sensitivity at a wavelength of 476 nm or in the vicinity of wavelength from 460 nm to 510 nm is measured to calculate the quantitative value of lithium.

In this case also, the sensitivity at a wavelength of 550 nm can be corrected by the following equation to cancel out an influence of hemoglobin:

> The sensitivity at a wavelength of 550 nm=the sensitivity at a wavelength of 550 nm for lithium-F28 tetraphenylporphyrin complex+the sensitivity at a wavelength of 550 nm for hemoglobin−the sensitivity at a wavelength of 600 nm for hemoglobin Advantages of Invention The concentration of lithium in an aqueous solution such as biological specimen and environmental sample can be determined or measured easily by using the lithium reagent composition according to the present invention and by using the method and device for measuring lithium ions according to the present invention. In the lithium reagent compositions defined in claims 1 to 11, the calibration curve of the concentration of lithium is linear in a practical range of from 0.0 to 2.0 mEq/L, so that the concentration can be calculated by a simple operation from numerical values of the colorimeter and of the ultraviolet-visible light spectrophotometer.

Therefore, the lithium concentration in biological specimen or serum sample can be determined quickly and quantitatively by usual spectrophotometer. The resulting data can be used as a management index in TDM treatment for example. Or, the quantitative determination of a larger number of specimens can be done in a short time by an automatic analyzer for clinical chemistry.

In the present invention, the lithium reagent composition is adjusted to a pH range of from pH 5 to pH 12 so as to enable measurement by the spectrometry. In fact, the chelating reagent according to the present invention (F28 tetraphenylporphyrin lithium) does not bond to helium ions in an acidic range of under pH 5, or change in color which is dependent to the lithium concentration is not observed in an acidic range of under pH 5. On the contrary, in an alkaline side of over pH 12, a color tone of the chelating reagent and of coloring complex formed is not stable.

The stability of the color tone becomes poor due to absorption of carbon dioxide in air which is a cause of pH fluctuation. In the pH range from pH 5 to pH 7, the chelating reagent bonds to lithium ions and hence the specific coloring of the chelating reagent can be observed. However, the coloring speed is too slow. Therefore, the pH range from pH 8 to pH 11 is preferable, since, in the pH range from pH 8 to pH11, the chelating reagent bonds to lithium ion rapidly and the coloring reaction is specific and stable.

Metal complex of tetraphenylporphyrin possesses a typical specific spectrum range in the vicinity from 380 nm to 460 nm called the "Soret band" in which the maximum sensitivity is obtained. This range may be selected as a measuring wavelength range. However, the sensitivity in this range is too high for a lithium concentration having clinical significance in a serum sample, so that dilution operation is necessary, resulting in increase of complicated operations and of additional units for dilution, which increase a size of measuring unit.

In the present invention, a wavelength of 550 nm or in the vicinity range of from 530 nm to 560 nm in which the sensitivity is lower by several times than that of the Soret band is used as the measuring wavelength range. By selecting this range, the optimum sensitivity is obtained for a concentration of sample to be tested and complicated dilution operation and dilution unit can be eliminated. Still more, the calibration curve according to the present invention has better linearity than that of in case of the Soret band, so that the concentration can be calculated easily from the measured values obtained by a simple colorimeter or an ultraviolet-visible light spectrophotometer. Still more, change in color tone is very sharp in the present invention, so that the level of concentration can be judged by visual observation or naked eyes.

If the Soret band is used as a photometry wavelength, there is such another problem that the quantitative value of lithium is influenced by the presence of other organic substances and color components such as nitrate ion, creatinine, bilirubin, biliverdine and hemolyses hemoglobin. This influence or problem can be reduced in the present invention and the concentration of lithium can be determined with high precision.

Precise measurement can be assured by canceling out an influence of hemoglobin by the following equation for the sensitivity at a wavelength of 550 nm:

> The sensitivity at a wavelength of 550 nm=the sensitivity at a wavelength of 550 nm for lithium-F28 tetraphenylporphyrin complex+the sensitivity at a wavelength of 550 nm for hemoglobin−the sensitivity at a wavelength of 600 nm for hemoglobin In the conventional method for measuring lithium, a large scale single purpose apparatus was required. In this invention, the concentration of lithium can be determined by a small portable colorimeter and can be constructed as a POCT kit.

BRIEF DESCRIPTION OF DRAWINGS

FIG. 1 Graph of lithium concentration-absorbance detected at a wavelength of 550 nm obtained in the result of Example 1 according to this invention.

FIG. 2 Table 1 showing a comparison of the lithium concentration of Reagent (C) containing triethanol amine used in Example according to the present invention to the lithium concentration obtained by using an automated analyzer (D). In Reagent (A), DMSO was used in place of triethanol amine and in Reagents (B), neither DMSO nor triethanol amine is used.

FIG. 3 Graph of lithium concentration-absorbance detected at a wavelength of 340 nm obtained in Example 1.

FIG. 4 Graph of lithium concentration-absorbance detected at a wavelength of 384 nm obtained in Example 1.

FIG. 5 Graph of lithium concentration-absorbance detected at a wavelength of 412 nm obtained in Example 1.

FIG. 6 Graph of lithium concentration-absorbance detected at a wavelength of 492 nm obtained in Example 1.

FIG. 7 Graphs showing change in spectrum at wavelength of 300 to 450 nm in the formation of F28 tetraphenylporphyrin-lithium complex according to this invention (the density is changed from 0.9 mM to 3.5 mM. The vertical axis indicates the absorbance and the horizontal axis indicates the wavelength)

FIG. 8 Graphs showing change in spectrum at wavelength of 450 to 600 nm in the formation of F28 tetraphenylporphyrin-lithium complex according to this invention FIG. 9 Table 2 showing a comparison between measured values obtained in Example 1 of the present invention and values of the control serum samples.

FIG. 10 Graph of lithium concentration-absorbance detected at a wavelength of 476 nm obtained in Example 2.

FIG. 11 Graph of lithium concentration-absorbance detected at a wavelength of 550 nm obtained in Example 3.

MODE FOR CARRYING OUT THE INVENTION

Inventors studied lithium reagent compositions which can be used for measuring a concentration of lithium in serum and blood plasma quantitatively and more simply, and focused on a compound represented by the general formula:

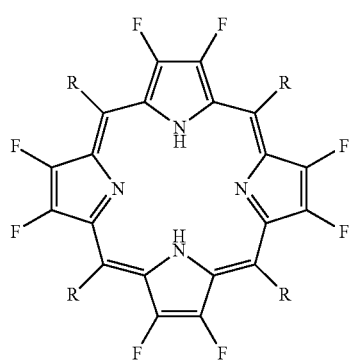

(I)

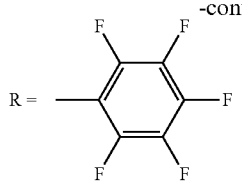

in which all of hydrogen atoms bonded to carbons of a tetraphenylporphyrin ring are replaced by fluorine atoms (the total number of fluorine is 28) in the macro cyclic compound disclosed in non-Patent Document 1. Inventors arrived at an invention disclosed in Patent Document 3 (Japanese Patent No. 5,222,432) in which an organic solvent is used.

Now, inventors found such a fact that a basic organic compound selected from monoethanol amine, di-ethanol amine and tri-ethanol amine can use to prepare an aqueous solution of F28 tetraphenylporphyrin, without using the organic solvent such as dimethyl sulfoxide (DMSO), dimethyl formamide (DMF) and dimethyl acetamide (DMA). The present invention is based on this finding.

Patent Documents 2 and 3 disclose similar lithium reagent compositions comprising a macro cyclic compound having pyrrole rings in which eight bromine atoms (Br) are boned to β position of the pyrrole ring, to provide an analytical reagent which can react with lithium ions. This compound, however, is difficult to react with lithium if pH is not in an alkali side above pH 11.

In case of the F28 tetraphenylporphyrin according to the present invention, the reaction occurs in a range of pH 5 to pH 12. In the present invention, the F28 tetraphenylporphyrin is used as a chelating reagent and is mixed with a basic organic compound selected from monoethanol amine, di-ethanol amine and tri-ethanol amine in place of the organic solvent, determine the quantity of lithium ions in an aqueous system.

Now, the lithium reagent composition according to the present invention is explained in much in details by using Examples.

EXAMPLES

Example 1 (Reagent 1)

Lithium reagent composition (Reagent 1) used in Example 1 contains following components (% by weight):

| | |
|---|---|
| Chelating reagent: F28 tetraphenylporphyrin: | 0.01 wt % |
| Multi-functional modifier triethanolamine | 1 wt % |
| Stabilizer (nonionic surfactant): Triton X-100 ® (polyoxyethylene octylphenyl ether) | 1. wt % |
| Stabilizer (anionic surfactant): (sodium dodecyl sulfate) | 1. wt % |
| Masking agent: EDTA-2K | 0.04 wt % |

To a mixture of above components, sodium hydroxide was added to adjust pH to pH 10.8 and purified water was added up to the total volume of 1 liter to obtain a lithium reagent composition containing no organic solvent.

This lithium reagent composition according to the present invention contains no organic solvent. The term "multi-functional modifier" is used because the above triethanolamine have several functions of dispersant, buffering agent, emulsifier and complexing agent and it is believed that the triethanolamine may have any one or more functions among them.

When measurement is carried out at pH 8, the reaction kinetics will become a little slow and quantitative stabilization is obtained after 10 to 20 minutes. At pH 10, the reaction completes within 10 minutes. Therefore, the lithium reagent composition according to the present invention can be handled without difficulty by using a buffer system of a pH range of pH 5 to 10 and hence there is no necessity to use a condensed buffer system such as aqueous solution of sodium hydroxide and of potassium hydroxide which was used when pH is higher than pH 11.

The pH value can be selected according to user's need but a sufficient reaction kinetics can be obtained at pH 10 in which a buffer system which can maintain sufficient buffer power such buffer system as Good's buffer, ammonium chloride and carbonic acid can be used.

Into 24 μL of the lithium reagent composition, 2 μL of a test sample containing lithium carbonate whose concentration is known was added. The resulting mixture was mixed sufficiently to effect a reaction at ambient temperature for 10 minutes and then an absorbance was measured at 550 nm by a microplate reader SH-1000 type of COLONA Co., Ltd. FIG. 1 shows the result which is a relation between the absorbance and Li concentration in the test sample.

The vertical axis of FIG. 1 indicates the absorbance and the horizontal axis indicates the Li concentration (mM) in the test sample. FIGS. 1, 3, 4, 5, 6, 10 and 11 show the same relation.

FIG. 1 shows such a fact that the absorbance increases and depends to the concentration of lithium in the test sample and draws a good approximation straight line (the linearity $r=0.992$). Thus, it is clear that a calibration curve can be obtained by using the lithium reagent composition according to the present invention obtained in Example 1 and a lithium standard sample.

Since the regression line shows a good linearity, the correct calibration of lithium concentration can be carried out by plotting two points of a lithium standard sample and of a blank.

No organic solvent was used in Example 1. Therefore, Example 1 is different from Patent Document 3 in which a water-soluble organic solvent such as dimethyl sulfoxide (DMSO), dimethyl formamide (DMF) and dimethyl acetamide (DMA) was used. Thus, we found such a fact that F28 tetraphenylporphyrin is an effective chelating agent in this Example 1. This fact was confirmed by following Experiments 1 and 2.

Experiment 1

In order to prove that the concentration of lithium in serum can be determined precisely, following three reagent compositions (A) to (C) were prepared by the same procedure as Example 1:
(A) a reagent composition containing dimethyl sulfoxide (DMSO) in place of triethanolamine of Example 1,
(B) a reagent composition containing neither dimethyl sulfoxide (DMSO) nor triethanolamine of Example 1, and
(C) a reagent composition containing triethanolamine of Example 1 but containing no dimethyl sulfoxide (DMSO).

Calibration curves were plotted by the same method as Example 1 under the same measuring condition as Example 1. Several serum samples having different lithium concentrations were used as test samples and the concentration of lithium in the test samples was determined.

FIG. 2 (Table 1) shows the results of measured values obtained when the above reagent compositions (A) to (C) were used. Table 1 shows also the results of measured values obtained when an automated analyzer is used (D) for comparison. Table 1 reveals such a fact that measured values obtained in the above reagent compositions (A) and (C) have good correlation with measured values obtained by the automated analyzer (D).

Thus, it was confirmed from Experiment 1 that the reagent composition (B) containing neither dimethyl sulfoxide (DMSO) nor triethanolamine induce no coloring even if the effective chelating agent of F28 tetraphenylporphyrin is included, and that the concentration of lithium in serum can be determined precisely in case of the reagent composition (C) containing triethanolamine according to the present invention but containing no dimethyl sulfoxide (DMSO).

Measuring Method

Here, we will explain a method and apparatus for measuring the concentration of lithium.

2 μl of a test sample was added to 240 μL of the reagent composition obtained in Example 1 to prepare a test solution having a pH value of 10.8. The test solution was reacted with test sample for 10 minutes at ambient temperature. The absorbance was measured by using a microplate reader SH-1000 type of COLONA Co., Ltd. at following different wave lengths (a) to (d), a reference being a blank containing no reagent composition:
(a) at a wavelength of 340 nm (FIG. 3)
(b) at a wavelength of 384 nm (FIG. 4)
(c) at a wavelength of 412 nm (FIG. 5)
(d) at a wavelength of 492 nm (FIG. 6)

The absorbance obtained at a wavelength of 550 nm is shown in FIG. 1. FIGS. 1, 3, 4, 5 and 6 show the results. The vertical axis indicates the absorbance and the horizontal axis indicates the Li concentration (mM) in serum.

FIG. 7 and FIG. 8 are graphs showing changes in spectrum when F28 tetraphenylporphyrin-lithium complex is formed at respective density (from 0.9 mM to 3.5 mM). In FIG. 7 and FIG. 8, the main measuring wavelength of 340 nm (FIG. 3), of 384 nm (FIG. 4), of 412 nm (FIG. 5), of 492 nm (FIG. 6) and of 550 nm (FIG. 1) are indicated by respective arrows. In FIG. 7 and FIG. 8, the vertical axis indicates the absorbance and the horizontal axis indicates the wavelength.

The maximum sensitivity for metal complex of tetraphenylporphyrin is obtained at a wavelength range of so-called Soret band (about from 380 nm to 460 nm). However, in the present invention, this Soret band range is not used but a wavelength of 550 nm or in the vicinity range of from 530 nm to 560 nm is used, so that complicated operations of dilution and dilution means or an auxiliary facility are not necessary in the present invention.

Still more, the better linearity of the calibration curve can be obtained when a wavelength of 550 nm or in the vicinity range of from 530 nm to 560 nm is used comparing to the Soret band of about from 380 nm to 460 nm, so that the precise concentration can be calculated easily by a simple colorimeter or spectrophotometer. Still more, since change in color from yellow to red is very sharp, the level of concentration can be detected easily by naked eyes.

In the conventional technique, an apparatus of large scale for exclusive use is necessary to measure the lithium concentration. In the present invention, the lithium concentration can be measured easily by a portable colorimeter or ultraviolet-visual light spectrophotometer which is used widely. The present invention can be constructed in a form of a POCT kit.

Now, we will describe one of the correction method for correcting an error of the method for measuring the lithium concentration according to the present invention.

It is known that there are two absorption peaks at about 540 nm and about 560 nm to 650 nm (β band and α band respectively) originated from hemoglobin as an interfering factor in test samples such as hemolyzed serum. If the reagent composition according to the present invention is contacted with a specimen containing a highly concentrated hemoglobin, a positive error will occur with respect to an actual measured value, because the absorption at 550 nm which is photometric wavelength of the present invention and the absorption at 540 nm caused by the β band and α band of hemoglobin overlap. Namely, the measured sensitivity at 550 nm=the sensitivity of lithium-F28 from tetraphenyl porphyrin complex at 550 nm+the sensitivity caused by hemoglobin at 550 nm=a positive error caused by hemoglobin.

The present inventor found such a fact that two sensitivities of hemoglobin at 550 nm and 600 nm are nearly identical. Namely, the sensitivity of hemoglobin at 550 nm=the sensitivity of hemoglobin at 600 nm. Thus, the present inventor found that the sensitivity of hemoglobin at 550 nm can be offset by the sensitivity of hemoglobin at 600 nm.

Therefore, a precise sensitivity at 550 nm can be calculated by correcting the sensitivity of hemoglobin at 550 nm by following equation:

The precise sensitivity at 550 nm=the sensitivity of lithium-F28 tetraphenylporphyrin complex at 550 nm+the sensitivity of hemoglobin at 550 nm−the sensitivity of hemoglobin at 600 nm The sensitivity of hemoglobin at 600 nm is preferably used as a correction value used in the above offsetting. However, it is possible to use neighbor wavelength around 600 nm which shows nearly same sensitivity at the center wavelength of 550 nm.

The measurement wavelength is preferably or mainly at 550 nm as mentioned above. However, as can be seen from spectrums of FIG. 7 and FIG. 8, the quantitative value of lithium can be calculated by the calculation means by measuring another wavelength than 550 nm. For example, the sensitivity at a wavelength of 570 nm, or at a wavelength in the vicinity of from 565 nm to 650 nm, or the sensitivity at a wavelength of 340 nm, or at a wavelength in the vicinity of from 310 nm to 350 nm, or the sensitivity at a wavelength of 380 nm, or at a wavelength in the vicinity of from 350 nm to 400 nm, or the sensitivity at a wavelength of 476 nm, or at a wavelength in the vicinity of from 460 nm to 510 nm can be used to calculate the quantitative value of lithium.

Experiment 2
Comparison of Measured Values for Control Serum Samples by Plate Reader The lithium concentration was measured for following control serum samples in which the lithium concentrations are valued:

Pathonorm L (SERO AS)
Pathonorm H (SERO AS)
Seronorm human (SERO AS)

2 μL of each test sample was added into 240 μL of the lithium reagent composition which was prepared by the same method as Example 1 to prepare a test solution having a pH value of 10.8. After a reaction was continued for 10 minutes at ambient temperature, the absorbance was measured by using a microplate reader SH-1000 type of COLONA Co., Ltd. at a wave lengths of 550 nm.

FIG. 9 (Table 2) shows the results of measured values when calibration was made by using a standard sample containing 0.86 mM of lithium ion (lithium carbonate). Table 2 reveals such a fact that measured values obtained by the lithium reagent composition of Example 1 prepared according to the present invention have good correlation with guaranteed values.

Example 2 (Reagent 2)

In another lithium reagent composition (Reagent 2) prepared in this Example 2, a proportion of triethanolamine was increased and proportions of the stabilizer and of the masking agent were a little changed. This lithium reagent composition (Reagent 2) contains following components (% by weight):

| | |
|---|---|
| Chelating reagent: F28 tetraphenylporphyrin: | 0.01 wt % |
| Multi-functional modifier triethanolamine | 3.7 wt % |
| Stabilizer (nonionic surfactant): Triton X-100 ® (polyoxyethylene octylphenyl ether) | 1.5. wt % |
| Stabilizer (anionic surfactant): (sodium dodecyl sulfate) | 1. wt % |
| Masking agent: EDTA-2K | 0.045 wt % |

This composition contains no organic solvent. Sodium hydroxide was added to the above lithium reagent composition to adjust pH to pH 10.8 and then, purified water was added up to the total volume of 1 liter to obtain a lithium reagent composition (Reagent 2) containing no organic solvent.

2 μL of a test sample containing lithium carbonate whose lithium concentration is known was added into 240 μL of the lithium reagent composition (Reagent 2) and stirred sufficiently. After a reaction was continued for 10 minutes at ambient temperature, the absorbance was measured by using a microplate reader SH-1000 type of COLONA Co., Ltd. at a wave lengths of 476 nm.

FIG. 10 shows the absorbance in the function of the lithium concentration of the test sample. FIG. 10 shows that the absorbance decrease in the function of the lithium concentration of the test sample and that good linearity is obtained. Or, a calibration curve can be made by using the lithium reagent composition (Reagent 2) of Example 2 and a lithium standard sample. Still more, the precise calibration of concentration can be done by plotting two points of the standard sample and of a blank.

Example 3 (Reagent 3)

This lithium reagent composition (Reagent 3) is different from Example 1 in that diethanolamine was used in place of triethanolamine. This lithium reagent composition (Reagent 3) contains following components (% by weight):

| | |
|---|---|
| Chelating reagent: F28 tetraphenylporphyrin: | 0.01 wt. % |
| Multi-functional modifier diethanolamine | 3.7 wt % |
| Stabilizer (nonionic surfactant): Triton X-100 ® (polyoxyethylene octylphenyl ether) | 1. wt % |
| Stabilizer (anionic surfactant): (sodium dodecyl sulfate) | 1. wt % |
| Masking agent: EDTA-2K | 0.04 wt % |

This composition also contains no organic solvent. The term "multi-functional modifier" is used in this composition also, because the above diethanolamine have several functions of dispersant, buffering agent, emulsifier and complexing agent and it is believed that the diethanolamine may have any one or more functions among them.

To a mixture of above components, sodium hydroxide was added to adjust pH to pH 10.8 and purified water was added up to the total volume of 1 liter to obtain a lithium reagent composition containing no organic solvent.

2 μL of a test sample containing lithium carbonate whose lithium concentration is known was added into 240 μL of the lithium reagent composition (Reagent 3) and stirred sufficiently. After a reaction was continued for 10 minutes at ambient temperature, the absorbance was measured by using a microplate reader SH-1000 type of COLONA Co., Ltd. at a wave lengths of 550 nm.

FIG. 11 shows the absorbance in the function of the lithium concentration of the test sample. FIG. 11 shows that the absorbance decrease in the function of the lithium concentration of the test sample and that good linearity is obtained. Or, a calibration curve can be made by using the lithium reagent composition (Reagent 3) of Example 3 and a lithium standard sample. Precise calibration of concentration can be done by plotting two points of the standard sample and of a blank. since a regression line shows good linearity.

As explained in the above Examples according to this invention, it was confirmed that an quantity of lithium in aqueous solutions such as biological specimens and environmental liquid samples can be determined by using a simple or small sized colorimeter and can be judged immediately by visual observation without using organic solvent such as dimethyl sulfoxide (DMSO), dimethyl formamide (DMF) and dimethyl acetamide (DMA).

Monoethanol amine also can be used although tri-ethanol amine and di-ethanol amine were used in Examples 1, 2 respectively. Monoethanol amine also have several functions of dispersant, buffering agent, emulsifier and complexing agent so that mono ethanolamine also is a multifunctional modifier.

The present invention relates also a measuring method and measuring apparatus using the reagent composition disclosed in Examples 1 to 3.

The present invention is not limited by special embodiments disclosed in Examples 1 to 3 but covers any variation unless it departs from the characteristics of the present invention.

The invention claimed is:

1. A reagent composition for detecting and measuring lithium, characterized in that it is in a form of an aqueous solution comprising a compound having a structure represented by the formula (I):

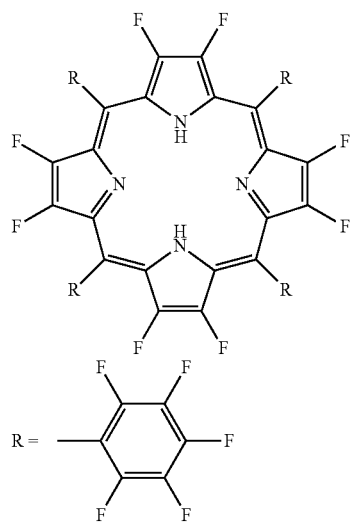

(I)

in which all hydrogens bonded to carbons of a tetraphenylporphyrin are replaced by fluorine atoms, mixed with a basic organic compound selected from monoethanol amine, di-ethanol amine and tri-ethanol amine and a pH modifier for adjusting the pH of the solution higher than pH 5.

2. The reagent composition for lithium according to claim 1, in which said pH modifier is selected from acids including hydrochloric acid, nitric acid, acetic acid, phosphoric acid, citric acid, carbonic acid, bicarbonate, oxalic acid and hydrochloric acid, alkali medicine including sodium hydroxide, potassium hydroxide and ammonia, and their salts.

3. The reagent composition for lithium according to claim 1, in which said pH modifier is pH buffer.

4. The reagent composition for lithium according to claim 3, in which said pH buffer is selected from citric acid, carbonic acid, bicarbonate, phosphoric acid, succinic acid, phthalic acid, ammonium chloride, sodium hydroxide, potassium hydroxide, as Good buffer, MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, CAPS, and their salts.

5. The reagent composition for lithium according to claim 1, in which the reagent composition develops a color for lithium in a pH range from pH 5 to pH 12.

6. The reagent composition for lithium according to claim 1, including further a stabilizer.

7. The reagent composition for lithium according to claim 6, in which said stabilizer is nonionic surfactant and/or anionic surfactant.

8. The reagent composition for lithium according to claim 7, in which said nonionic surfactant is selected from esters of sorbitan fatty acid, partial esters of pentaerythritol fatty acid, esters of propylene glycol fatty acid, glycerin fatty acid monoester, polyoxyethylene alkyl ether, polyoxyethylene alkyl phenyl ether, polyoxyethylene polyoxypropyleneglycol, partial esters of polyoxyethylene fatty acid, partial esters of polyoxyethylene sorbitol fatty acid, esters of polyoxyethylene fatty acid, fatty acid di-ethanol amide, fatty acid monoethanol amide, polyoxyethylene fatty acid amide, polyoxyethylene octylphenyl ether (TritonX-100®), p-nonyl phenoxypolyglycidol and their salts.

9. The reagent composition for lithium according to claim 7, in which said anionic surfactant is alkyl sulfate ester salt including sodium dodecyl sulfate, polyoxyethylene alkyl ether sulfate salt including sodium polyoxyethylene phenyl ether sulfate, alkyl benzene sulfonate including sodium dodecyl benzene sulfonate, and alkanesulfonate.

10. The reagent composition for lithium according to claim 8, including further a masking reagent.

11. The reagent composition for lithium according to claim 10, in which said masking reagent is chosen from ethylenediamine, N,N,N',N'-tetrakis (2-pyridylmethl)ethylenediamine (TPEN), pyridine, 2,2-bipyridine, propylenediamine, diethylenetriamine, diethylenetriamine-N,N,N',N'', N''-penta acetate (DTPA), triethylenetetramine, triethylenetetramine-N,N,N',N'',N''', N'''-hexaacetate (TTHA), 1,10-phenanthroline, ethylenediamine tetraacetate (EDTA), O,O'-bis(2-aminophenyl)ethylene glycol-N,N', N'-tetraacetate (BAPTA), N,N-bis(hydroxyethyl)glycine (Bicine), trans-1,2-diaminocyclohexane-N,N,N',N'-tetraacetate (CyDTA), O,O'-bis(2-aminoethyl) ethyleneglycol-N, N',N'-tetraacetate (EGTA), N-(2-hydroxyl)iminodiacetate (HIDA), iminodiacetic acid (IDA), nitrilotriacetic acid (NTA), nitrylotrismethylphosphonate (NTPO) and their salts.

* * * * *